United States Patent [19]

Kim et al.

[11] Patent Number: 5,658,913

[45] Date of Patent: Aug. 19, 1997

[54] CHEMOPREVENTIVE COMPOUNDS AND A PREPARATION METHOD AND USE THEREOF

[75] Inventors: Nak Doo Kim, 302-304, Shinbanpo Apartment Chamwon-dong, Socho-ku, Seoul 137-030; Jong Wook Lee, Kwacheon; Sang Geon Kim, Seoul; Young Ro Choi, Euiwang, all of Rep. of Korea

[73] Assignee: Nak Doo Kim, Seoul, Rep. of Korea

[21] Appl. No.: 454,160

[22] PCT Filed: Oct. 21, 1994

[86] PCT No.: PCT/KR94/00144

§ 371 Date: Jun. 15, 1995

§ 102(e) Date: Jun. 15, 1995

[87] PCT Pub. No.: WO95/11236

PCT Pub. Date: Apr. 27, 1995

[30] Foreign Application Priority Data

Oct. 21, 1993 [KR] Rep. of Korea ............... 1993/21876

[51] Int. Cl.⁶ ............... A61K 31/495; C07D 241/18; C07D 409/12
[52] U.S. Cl. ............... 514/255; 514/252; 544/405; 544/408
[58] Field of Search ............... 544/405, 408; 514/255, 252

[56] References Cited

U.S. PATENT DOCUMENTS 3,931,166  1/1976  Winter et al. ............... 544/405
3,989,713  11/1976  Winter et al. ............... 549/498
4,105,661  8/1978  Winter et al. ............... 544/405
4,123,613  10/1978  Bernardi et al. ............... 544/408

FOREIGN PATENT DOCUMENTS 1390329  4/1973  United Kingdom .

OTHER PUBLICATIONS

Bourguignon et al, *Chemical Abstracts*, vol. 93, No. 150209 (1980).

Sato et al, *Chemical Abstracts*, vol. 118, No. 212 276 (1993).

Shimazaki et al, *Heterocycles*, 27, pp. 1643–1651 (1988).

The Pyrazines by G.B. Barlin, pp. 196–197 (1982).

*Primary Examiner*—Emily Bernhardt
*Attorney, Agent, or Firm*—Oblon, Spivak, McClelland, Maier & Neustadt, P.C.

[57] ABSTRACT

Disclosed herein is a compound having formula (I), wherein $R_1$ represents a hydrogen atom or a $C_{1-3}$ alkyl group; and $R_2$ represents phenyl and furanyl group, or a group represented by the formula: $-C(R_a)=C(R_b)(R_c)$, wherein $R_a$, $R_b$, and $R_c$, being the same or different from each other, means hydrogen atom or methyl or phenyl group. The present invention further provides a method for preparing the compound (I) and a composition comprising as an active ingredient the compound (I). The compound (I) of the present invention can effectively inhibit the expression of enzymes involved in phase I reaction while activating the expression of enzymes involved in phase II reaction, thereby can be advantageously used to protect liver from being injured by various chemicals.

7 Claims, 10 Drawing Sheets

Group No.  1  2  3  4  5  6  7

Group 1 :   Control
Group 2 :   1 day  administration of pyrazine
Group 3 :   2 days administration of pyrazine
Group 4 :   3 days administration of pyrazine
Group 5 :   1 day  administration of compound(Ex. 1-1)
Group 6 :   2 days administration of compound(Ex. 1-1)
Group 7 :   3 days administration of compound(Ex. 1-1)

FIG. 5

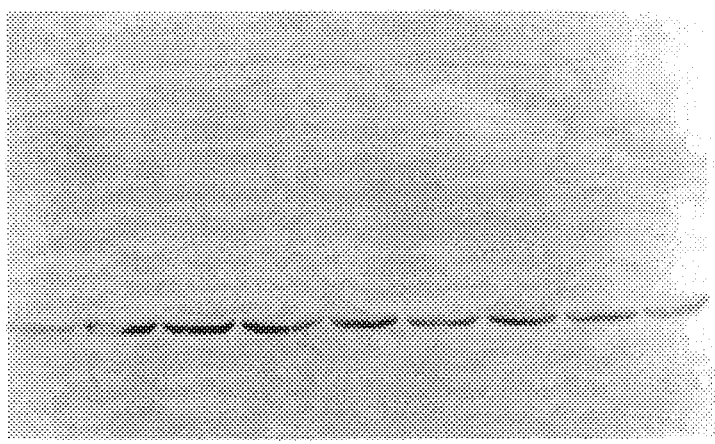

Group No.  1  2  3  4  5  6  7  8  9

Group 1 :   Control
Group 2 :   INAH -administered group
Group 3 :   INAH + Ex. 2 compound -administered group
Group 4 :   INAH + Ex. 3 compound -administered group
Group 5 :   INAH + Ex. 4 compound -administered group
Group 6 :   INAH + Ex. 5 compound -administered group
Group 7 :   INAH + Ex. 6 compound -administered group
Group 8 :   INAH + Ex. 7 compound -administered group
Group 9 :   INAH + Ex. 8 compound -administered group Group No.   1   2   3   4   5   6   7

Group 1 :   Control
Group 2 :   1 day administration of pyrazine
Group 3 :   2 days administration of pyrazine
Group 4 :   3 days administration of pyrazine
Group 5 :   1 day administration of compound(Ex. 1-1)
Group 6 :   2 days administration of compound(Ex. 1-1)
Group 7 :   3 days administration of compound(Ex. 1-1)

Group No.    1    2    3    4    5    6    7    8

Group 1 :   Control
Group 2 :   Ex. 2 compound -administered group
Group 3 :   Ex. 3 compound -administered group
Group 4 :   Ex. 4 compound -administered group
Group 5 :   Ex. 5 compound -administered group
Group 6 :   Ex. 6 compound -administered group
Group 7 :   Ex. 7 compound -administered group
Group 8 :   Ex. 8 compound -administered group

CHEMOPREVENTIVE COMPOUNDS AND A PREPARATION METHOD AND USE THEREOF

This application is a 371 of PCT/KR 94/0144 filed Oct. 21, 1994.

BACKGROUND OF THE INVENTION

1. Field of the Invention

The present invention relates to a novel useful compound, a use thereof and a preparation method thereof. More particularly, it relates to a novel compound having chemopreventive activity and to a method for preparing the same and a composition comprising the same as an active ingredient.

2. Description of the Prior Art

A living body has functions to excrete xenobiotics by inactivating them or reducing lipophilicity thereof to transform into hydrophilic substances. These functions are performed by mediation of various enzymes and may be classified depending on the kind of enzymes into two groups: Phase I reaction(oxidation, reduction and hydrolysis, etc) and phase II reaction(conjugation). Sometimes, these functions are adversely performed to form a more reactive compound which may cause damages to macromolecules in the cells, thus inducing cancer formation.

Particularly, cytochromes P-450(CYP 450), which are present in smooth endoplasmic reticulum of hepatic cells and other cells, are an oxidation enzymes involved in phase I reaction. Cytochromes P-450 oxidize steroids, fatty acids and amines which are synthesized in a living body as well as metabolize medicines, chemical carcinogens and mutagens to more hydrophilic execretable substances.. Nevertheless, cytochromes P-450 sometimes activate xenobiotics, which causes damages to macromolecules and consequently induce a cancer formation(Black, S. D., Coon, M. J., P-450 cytochromes: Structure and function, Adv. Enzymol., 60:35–87(1987)). Cytochromes P450 are classified into gene families and sub families depending on the similarity of base sequence. Among the multiple forms of P-450, cytochrome P-450 2E1 has a very high substrate specificity to a wide spectrum of exogenous substances and enhances the toxicity of the exogenous substances by activating them.

For example, therapeutically effective dose of acetaminophen causes hepatotoxicity in a chronic alcoholics, because cytochrome P-450 2E1 activate acetaminophen with a high substrate specificity and the activated acetaminophen attacks macromolecules such as proteins to cause hepatic necrosis(Wrighton, S. A., Thomas, P. E., Molowa, D. T., Haniu, M, Guzelian P. S., Characterization of ethanol-inducible human liver N-nitrosodimethylamine demethylase, Biochemistry, 25; 6731–6735(1986)).

For the metabolism of carbon tetrachloride which cause hepatic necrosis, it is reported that an increase in the level of reactive metabolites is closely related to an increase of expression of cytochrome P-450 2E1 (Ansher, S. S. Dolan, P., Bueding E., Chemoprotective effects of two dithiolthiones and butylhydroxyanisole against carbon tertrachloride and acetaminophen toxicity, Hepatoloty, 3; 932–935(1983)). It also plays an important role in activating xenobiotics due to a high affinity to nitrosamine, a precursor carcinogen (Peng, R., Yang, C. S., The induction and competitive inhibition of a high affinity microsomal nitrosodimethy-lamine demethylase by ethanol, Carcinogenesis, 3; 1457–1461(1982)).

Benzene is known to induce a leucopenia, a leukemia and an agranulocytic anemia and it has been reported that cytochrome P-450 2E1 is involved in the metabolism of benzene(Lewis, J. G., Stewart, W., Adams, D. C., Role of oxygen radicals in induction of DNA damage by metabolite of benzene, Cancer Res., 48;4762–4765(1988)). Recently, it has been reported that this enzyme shows a very high substrate specificity to halothane, a inhaling anesthetic so that causes a hepatotoxicity. This is due to the fact that the increased trifluoroacetyl free radicals formed from intermediates form adducts with liver proteins to produce neoantigens(Kenna, J. G., Pohm, L. R., Factors affecting the expression of trifluoroacetylated microsomal protein neoantigen in rats treated with halothane, Drug Metab. Dispos., 18;788–792(1990)).

Moreover, cytochrome P-450 2E1 is closely related to hepatotoxicity enhancements by activating various low molecular weight organic substances such as isoniazid, ethanol, acetone. p-nitrosodimethylamine, nitrosoamine, phenol, pyridine, pyrazole, p-nitrophenol, aniline or diethylether. Cytochrome P-450 2E1 may also be induced by a fasting or diseases such as diabetes.

On the other hand, the enzymes involved in phase II reactions, for example glutathione S-transferase(hereinafter, "GST") and microsomal epoxide hydrolase(hereinafter "mEH") have a role of detoxicating the exogenous toxic substances. These enzymes detoxicate the exogenous toxic substances in various ways, for example a different isoenzymes of GST transfer a thiol group from glutathione to elecrophilic receptors and mEH hydrate oxides. Therefore, an increase in the amount of such enzymes can play an important role in protecting tissues from oxidative damages and environmental stresses(Pickett, C. B., Lu, A. Y. H., Glutathione S-transferase; Gene structure, regulation and biological function, Annu. Rev. Biochem., 58; 743–764 (1989) and Seidegrad, J, DePierre, J. W., Microsomal epoxide hydrolase properties, regulation and function, Biochim. Biophys. Acta., 695; 251–270(1983)).

Therefore, a cancer induction and toxicity due to an activation of xenobiotics can be prevented by modulating the metabolism, that is to say by inhibiting the phase I reactions to inhibit a formation of activated toxic intermediates and by enhancing the phase II reactions to promote the excretion of toxic substances. Extensive researches have been made to provide a chemopreventive agent having a metabolism-modulating activity described above. As a result thereof, there are reported some compounds having a chemopreventive activity.

For example, butylhydroxyanisole, a food antioxidant, shows an anti-cancer activity by inducing enzymes involved in phase II reactions(Cha, Y. N., Bueding, E., Effect of 2(3)-tert-butyl-4-hydroxyanisole administration on the activities of several hepatic microsomal and cytoplasmic enzymes in mice, Biochem. Pharmacol., 28;1917–1921 (1979)), and butylhydroxytoluene also shows a anti-cancer activity by inducing enzymes involved in phase II reactions (Cha, Y. N., and Heine, H. S., Comparative effects of dietary administration of 2(3)-tert-butyl-4-hydroxyanisole and 3,5-ditert-butyl-4-hydroxytoluene on the several hepatic enzyme activities in mice and rat, Cancer Res., 42; 2609–2615(1982) ).

Pyrazine, a component of naturally occurring or synthetic medicines such as pyrazinamide or oltipraz has been reported to have an activity of inducing cytochrome P-450 2E1, an enzyme involved in phase I reaction as well as GST and mEH, enzymes involved in phase II reaction(Novak, R.

F., Kim, S. G., Brooks, S. C., Primiano, T., Slinas, F. and Novak, J. C., Thiazole, pyridazine and pyrazine induction of glutathione S-transferase of rat, Toxicologist, 11;48(1990)). Oltipraz, which contains pyrazine in the molecule, also has an ability of inducing enzymes of phase II reactions so that it can suppress lung and stomach cancers.

However, these substances have an ability to induce enzymes of phase II reactions but not show any inhibition activity against enzymes of phase I reactions.

On the other hand, allysulfide, a component of garlic oil, has been reported to strongly suppress liver and colon cancers by inhibiting the expression of cytochrome P-450 2E1 which activates a precursor carcinogen, nitrosoamine (Brady, J. F., Li, D, Ishzaki, H and Yang, C. S., Effect of diallylsulfide on rat liver microsomal nitrosoamine metabolism and other monooxygenase activities, Cancer Res., 48;5937–5940(1988) and Hayes, M. A., Rushmore, T. H. and Goldberg, M. T., Inhibition of hepatocarcinogenic responses to 1,2-dimethylhydrazine by diallylsulfide, a component of garlic oil, Carcinogenesis, 8;1155–1157(1987)). Moreover, the present inventors have shown that allylsulfide strongly inhibits the expression of cytochrome P-450 2E1 and further completely suppress cytochrome P-450 2E1 induced by the action of pyrazine(Biochemical pharmacology, (submitted) 1993).

However, there is no effective chemopreventive agent which inhibits the phase I reaction enzymes as well as induce the phase II reaction enzymes.

The present inventors made extensive researches to provide a chemopreventive agent which inhibits the expression and activities of the phase I reaction enzymes as well as induce the phase reaction enzymes and restore them from the inhibition by the inhibitory materials such as isoniazid. As results thereof, we accomplished the present invention.

SUMMARY OF THE INVENTION

Thus, an object of the invention is to provide a novel pyrazine derivatives which can inhibit the phase I reaction enzymes to prevent the formation of activated toxic intermediate metabolites as well as induce the phase II reactions to promote the secretion of toxic substances.

The other object of the invention is to provide a novel compound having the following formula(I):

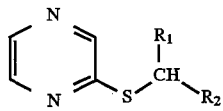

wherein, $R_1$ represents hydrogen atom or a $C_{1-3}$ alkyl group; and $R_2$ represents phenyl or furanyl group, or a group represented by the formula: $-C(R_a)=C(R_b)(R_c)$, wherein $R_a$, $R_b$, and $R_c$, being the same or different from each other, means hydrogen atom or methyl or phenyl group.

The other object of the invention is to provide a process for preparing the compound(I), which comprises reacting the compound of the formula(II):

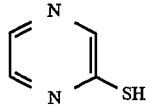

with the compound of the formula(III):

wherein,

X represents a halogen atom or a hydroxyl group; and $R_1$ and $R_2$ have the same meanings defined as above.

The another object of the invention is to provide a pharmaceutical composition for protecting liver from the chemicals which may injure liver comprising as an active ingredient the compound(I).

The other objects and applications of the present invention shall be apparent to the skilled in the art by the following detailed description of the invention.

BRIEF DESCRIPTION OF THE DRAWINGS

FIG. 5 is immunoblot analyses of microsomes isolated from rats treated with corn oil, INAH, INAH plus the present compound with anti-P450 2E1 antibody(Experimental Example 2).

DETAILED DESCRIPTION OF THE INVENTION

Figure 1:
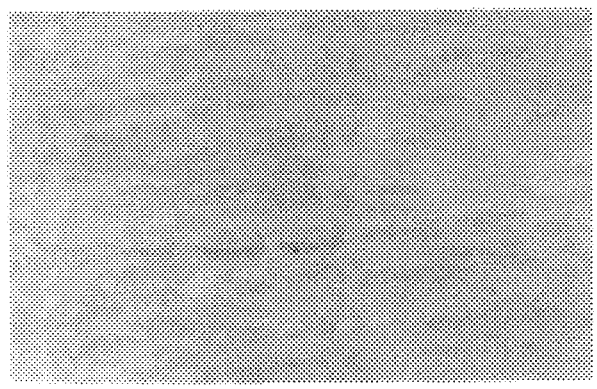
FIG. 1 is immunoblot analyses of hepatic microsomes from rats treated with corn oil, pyrazine and the present compound with anti-P450 2E1 antibody(Experimental Example 1(1)).

The term employed herein "chemopreventive" means that a compound can suppress the phase I reaction to prevent the formation of activated toxic intermediate metabolites as well as increase the phase II reaction to promote the secretion of toxic substances. The compounds of the present invention are effective in the presence of the inducer of phase I reaction or inhibitor of phase II reaction and consequently can effectively prevent liver from being injured by various chemicals.

According to the present invention, there is provided novel pyrazine derivatives having the following formula(I):

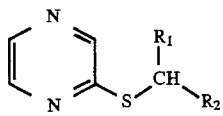

wherein, $R_1$ represents hydrogen atom or a $C_{1-3}$ alkyl group; and
$R_2$ represents phenyl or furanyl group, or a group represented by the formula: $-C(R_a)=C(R_b)(R_c)$, wherein $R_a$, $R_b$, and $R_c$, being the same or different from each other, means hydrogen atom or methyl or phenol group.

Among others, the compounds(I) wherein $R_1$ is hydrogen atom or methyl group, and $R_2$ is a group represented by the formula: $-C(R_a)=C(R_b)(R_c)$, wherein $R_a$, $R_b$, and $R_c$, being the same or different from each other, means hydrogen atom or methyl group are preferred.

Most preferred compounds(I), which show a high chemopreventive activity are listed in Table 1 below.

TABLE 1

| Compound | $R_1$ | $R_2$ |
|---|---|---|
| 1 | H | $-CH=CH_2$ |
| 2 | H | $-C_6H_5$ |
| 3 | H | $-CH=C(CH_3)_2$ |
| 4 | H | $-CH=CH(C_6H_5)$ |
| 5 | H | 2-furanyl |
| 6 | H | $-CH_2C(CH_2)(CH_3)$ |
| 7 | H | $-CH=C(CH_3)$ |
| 8 | Methyl | $-CH=CH_2$ |

According to the invention a method of preparing the compound(I) is provided.

The method comprises reacting the compound(II):

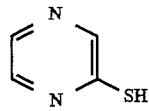

with the compound(III):

wherein,

X represents a halogen atom or a hydroxyl group; and $R_1$ and $R_2$ have the same meanings defined as above.

When the compound(III) wherein X is a halogen atom is reacted with the compound(II), the reaction may be carried out in the presence of a base in an inert solvent, for example N,N-dimethylformamide or N,N-dimethylaceteamide. The base employed in the invention may include, but not limited thereto, for example triethylamine, trimethylamine, N,N-dimethylaniline or diazabicycloundecene. The reaction temperature may vary between 0° C. to 100° C., preferably 30° C. to 80° C. The reaction time is in the range between 1 to 5 hours.

When the compound(III) wherein X is a hydroxyl group is employed, the compound(III) is treated with an organic phosphine such as triphenylphosphine in an inert solvent, for example N,N-dimethylformamide, dichloromethan, chloroform or tetrahydrofuran to form a intermediate, which is reacted with the compound(II). For this purpose, the compound(II) is dissolved in an inert solvent such as N,N-dimethylaceteamide by the aid of an organic base, for example triethylamine, trimethylamine or N,N-dimethylaniline.

The present invention further provides a pharmaceutical composition comprising the compound(I) as an active ingredient. The composition may contain a pharmaceutically acceptable conventional carrier or vehicles. The composition may be formulated by following the common techniques to solid, liquid or powder forms.

The formulation techniques and the additives, which are commonly employed in the pharmaceutical field, are not limited by the invention and may be chosen without difficulty by the skilled in the art.

The compound(I) may be administered into human beings or animals via non-limiting routes. Although the amount of the compound(I) may vary depending on the administration route, age and symptoms, or purposes, it may be selected from the range between 50 and 500 mg/kg, preferably between 100 and 300 mg/kg.

The following Examples will describe in more detail the present invention, but are not intended in any way to limit the present invention.

REFERENCE EXAMPLE 1

Preparation of 2-mercaptopyrazine 5.0 g of 2-chloropyrazine was dissolved in 40 ml of dimethylformamide and 5.0 g of NaSH.xH$_2$O was added thereto. The mixture was heated to 60° C. for 2 hours and cooled to 5° C. The resulting precipitates were filtered and 400 ml of diethylether was added to the filtrate. The precipitates were washed with diethylether and dried to give 3.0 g of yellow solid.

IR(KBr): 1650, 1570, 1562, 1425cm$^{-1}$ NMR(DMSO-d$_6$) ppm: 7.60(d, 1H), 7.80(d, 1H), 8.55(s, 1H), 14.35(bs, 1H)

EXAMPLE 1-1

Preparation of 2-(2-propenylthio)pyrazine 6.57 g of 2-mercaptopyrazine prepared in Reference Example 1 was dissolved in 80 ml of dimethylformaind and 8.6 ml of triethylamine was added thereto. 6.84 ml of allyl bromide was added to the solution and the mixture was stirred at 50° C. for 2 hours. 500 ml of ice water was added to the reaction solution and the resulting mixture was extracted with diethylether and concentrated. The residues were distilled under vacuum to give 7.85 g(85%) of oily pale yellow liquid.

bp. 0.5 torr/68°~69° C.

IR(Paraffin oil): 1700, 1633, 1559, 1506cm$^{-1}$

NMR(DMSO-d$_6$) ppm: 3.77(d, 2H), 5.10(d, 1H), 5.30(d, 1H), 5.81–6.02(m, 1H), 8.33(s, 1H), 8.48(s, 1H), 8.60 (s, 1H)

EXAMPLE 1-2

Preparation of 2-(2-propenylthio)pyrazine

The same procedure as that of Example 1-1 was carried out except that allyl chloride was employed instead of allyl bromide to give the title compound.

bp. 0.5 torr/68°~69° C.

IR(Paraffin oil): 1700, 1633, 1559, 1506cm$^{-1}$

NMR(DMSO-d$_6$) ppm: 3.77(d, 2H), 5.10(d, 1H), 5.30(d, 1H), 5.81–6.02(m, 1H), 8.33(s, 1H), 8.48(s, 1H), 8.60 (s, 1H)

EXAMPLE 1-3

Preparation of 2-(2-propenylthio)pyrazine 0.58 g of allyl alcohol was dissolved in 50 ml of dichloromethan and 2.89 g of triphenylphosphine and 1.96 g of N-bromosuccinimide were added thereto. The mixture was stirred at room temperature for 30 minutes, and 5 ml of dimethylformamide solution in which 1.0 g of 2-mercaptopyrazine and 1 ml of triethylamine were dissolved was added to the above solution. The resulting mixture was stirred at room temperature for 1 hour and poured into 100 ml of water. The organic layer was separated and concentrated to dryness. The residues were purified by silica gel chromatography using ethyl acetate:n-hexane=1:1 as an eluate to give 0.6 g of titled compound.

bp. 0.5 torr/68°~69° C.

IR(Paraffin oil): 1700, 1633, 1559, 1506cm$^{-1}$

NMR(DMSO-$d_6$) ppm: 3.77(d, 2H), 5.10(d, 1H), 5.30(d, 1H), 5.81–6.02(m, 1H), 8.33(s, 1H), 8.48(s, 1H), 8.60 (s, 1H)

EXAMPLE 2

Preparation of 2-(benzylthio)pyrazine

The same procedure as that of Example 1-1 was carried out except that benzyl bromide was employed instead of allyl bromide and silica gel column chromatography purification was carried out using ethyl acetate:n-hexane=1:5 as an eluate to give the titled compound.

mp. 65°~67° C. (white solid)

IR(KBr): 1500, 1445, 1380cm$^{-1}$

NMR(DMSO-$d_6$) ppm: 4.45(s, 2H), 7.2–7.35(m, 5H), 8.2–8.35(m, 3H)

EXAMPLE 3

Preparation of 2-(3-methyl-2-butenylthio)pyrazine

The same procedure as that of Example 1-3 was carried out except that prenyl alcohol was employed instead of allyl alcohol to give the titled compound as an oily liquid.

IR(Paraffin oil): 1501, 1375cm$^{-1}$

NMR(CDCl$_3$) ppm: 1.74(s, 6H), 3.81(d, 2H), 5.35(m, 1H), 8.2, 8.35, 8.4(m,3H)

EXAMPLE 4

Preparation of 2-(cinnamylthio)pyrazine

The same procedure as that of Example 1-3 was carried out except that cinnamyl alcohol was employed instead of allyl alcohol to give the titled compound as a white solid.

IR(Paraffin oil): 1490, 1440, 1380cm$^{-1}$

NMR(CDCl$_3$) ppm: 4.04(d, 2H), 6.35(tt, 1H), 6.6(d, 1H), 7.2–7.4(m, 5H), 8.2, 8.4, 8.47(m, 3H)

EXAMPLE 5

Preparation of 2-(furfurylthio)pyrazine

The same procedure as that of Example 1-3 was carried out except that furfuryl alcohol was employed instead of allyl alcohol to give the titled compound as an oily liquid.

IR(Paraffin oil): 14501, 1456, 1382cm$^{-1}$

NMR(CDCl$_3$) ppm: 4.46(s, 2H), 6.26(m, 2H), 7.34(d, 1H), 8.2, 8.4, 8.45(m, 3H)

EXAMPLE 6

Preparation of 2-(3-methyl-3-butenylthio)pyrazine

The same procedure as that of Example 1-3 was carried out except that 3-methyl-3-butene-1-ol was employed instead of allyl alcohol to give the titled compound as an oily liquid.

IR(Paraffin oil): 1500, 1450, 1370cm$^{-1}$

NMR(CDCl$_3$) ppm: 1.80(s,3H), 2.42(t, 2H), 3.3(t, 2H), 4.8(d, 2H), 8.2, 8.4, 8.45(m, 3H)

EXAMPLE 7

Preparation of 2-(2-butenylthio)pyrazine

The same procedure as that of Example 1-3 was carried out except that 2-butene-1-ol was employed instead of allyl alcohol to give the titled compound as an oily liquid.

IR(Paraffin oil): 1502, 1455, 1381cm$^{-1}$

NMR(CDCl$_3$ppm: 1.7(d, 3H), 3.8(d, 2H), 5.6(m, 2H), 8.2, 8.4, 8.45(m, 3H)

EXAMPLE 8

Preparation of 2-(3-butenylthio)pyrazine

The same procedure as that of Example 1-3 was carried out except that 3-butene-2-ol was employed instead of allyl alcohol to give the titled compound as an oily liquid.

IR(Paraffin oil): 1502, 1475, 1380cm$^{-1}$

NMR(CDCl$_3$) ppm: 1.4(d, 3H), 4.4(m, 1H), 5.0(d, 1H), 5.2(d, 1H), 5.9(m, 1H), 8.14, 8.3, 8.35(m, 3H)

EXPERIMENTAL EXAMPLE 1

Inhibition of the phase I reaction(1)

(1) Western blot analysis

In order to examine the effect of the compounds of the present invention on the expression of the enzymes involved in phase I reaction, the western blot analysis was carried out as follows:

28 Male sprague-Dawley rat weighing 190±30 g were divided into 7 groups. To the first group as a control group, 0.1 ml of corn oil per 200 g body weight was administered intraperitoneally. The second to fourth groups were administered intraperitoneally pyrazine dilluted with corn oil in a dose of 200 mg/kg body weight for 1, 2 or 3 days, respectively. The fifth to seventh groups were administered intraperitoneally the compound prepared in Example 1-1, which is diluted with corn oil in a dose of 200 mg/kg body weight for 1, 2 or 3 days, respectively. The test compounds were administered around 11 a.m.

The rats were prohibited from receiving food for 18 hours after administrating test compound and sacrificed by cervical dislocation around 7 to 8 a.m. the next day. Just after the death, physiological saline was perfused through hepatoportal vein to remove blood from, the liver tissue. The liver was removed and finely minced. Four volume times of 0.1M. Tris.HCl buffer(pH 7.4) was added and the liver tissue was homogenized. All steps were carried out at a constant temperature of 4° C. The homogenized tissue was centrifuged at 12,000 g for 20 minutes and the supernatant was ultra-centrifuged at 105,000 g for 1 hour to separate cytosol as a supernatant from the microsomes as a precipitate. Thus obtained microsomes were distributed in 0.1M Tris.KCl buffer and clarified by ultra-centrifuged at 105,000 g for 1 hour to give pure hepatic microsomes.

Thus separated microsomes were subjected to immunoblotting on the sodium dodecylsulfate-polyacrylamide gel electrophoresis(hereinafter, "SDS-PAGE") according to the method of Laemmli(Laemmli, U. K. Cleavage of structural proteins during assembly of the head of the bacteriophage T4, Nature, 227: 680–685, 1970).

BioRad Mini Protein II was employed and the gel was prepared as follows:

The separating gel was prepared by mixing 4.9 ml of second distilled water, 2.5 ml of 1M Tris buffer(pH 8.8), 50 μl of 20% sodium dodecylsulfate(SDS) and 2.5 ml of mixture of 30% acrylamide and 0.8% bisacrylamide, degassing the vessel using vacuum, adding 50 μl of 10% ammonium persulfate and 5 μl of N,N,N',N'-tetramethylethylenediamine, and allowing the resulting mixture to stand for 1 hour between two glass plates to obtain a gel.

The stacking gel was prepared by mixing 7.35 ml of second distilled water, 1.25 ml of 1.5M Tris buffer(pH 6.8), 50 μl of 20% SDS and 1.3 ml of mixture of 30% acrylamide and 0.8% bisacrylamide, degassing the vessel using vacuum, adding 50 μl of 10% ammonium persulfate and 10 μl of N,N,N',N'-tetramethylethylenediamine, and allowing the resulting mixture to stand for 1 hour between two glass plates to obtain a gel.

The microsomes from the first, second and third groups were diluted with a sample buffer(1M Tris(pH 6.8) 2.5 ml, 80% glycerol 5 ml, 20% SDS 5 ml, 1% bromophertolblue 0.2 ml, β-mercaptoethanol 2 ml and second distilled water 5.3 ml) and heated to 100° C. for 5 minutes. The dilution rate was determined so that each sample contains 20 μg of cytochrome P-450 2E1 per 7 μl.

The samples were spotted on the gel and electrophoresed using a running buffer(3.04 g of Tris, 14.42 g of glycine and 5 ml of 20% ADS in 1 l). The applied power is 12.5 mA for stacking gel and 20 mA for running gel.

After completion of the electrophoresis, gels were subjected to Western blot analysis according to the method of Davis(Davis, L. G., Dibner, M. D., Batey, J. F. Basic methods in molecular biology, New York, Elsevier, 311–314 (1986)). The gels were transferred to nitrocellulose paper by using BioRad Mini Trans-blot at 70 volts for 2 hours. The transfer buffer is prepared by dissolving 3.04 g of Tris, 14.42 g of glycine and 200 ml of methanol in 1 l of distilled water. After completion of the transfer, nitrocellulose paper was washed with water and immersed in 3% defatted milk solution at 4° C. overnight. Then, it was washed with physiological saline and subjected to immunochemical analysis as follows:

14 μl of Goat anti-rabbit P-450 2E1 IgG was mixed with 15 ml of PBS and placed into a bag containing the above-treated nictrocellulose paper, which was shaken for 2 hours. 15 μl of Biotinylated donkey anti-goat IgG in 15 ml of PBS was added to the nitrocellulose paper washed with PBS and reacted for 2 hours. The reaction mixture was washed with PBS and 1 μl of streptavidine-horseradish peroxidase in 15 ml of PBS was added. After reaction for 1 hour, 4-chloro-1-naphtol(1 mg/ml methanol) and 15 μl of hydrogen peroxidase were added to the reaction mixture. After about 30 seconds, when a color development was observed, the mixture was washed with deionized water to stop the reaction.

The results are shown in FIG. 1. The pyrazine-administration group, namely the second to fourth groups showed a significant increase in the expression of P-450 2E1 in proportional to the administration period. However, the fifth to seventh group which were received the compound of Example 1-1 showed a considerable decrease in the expression of P-450 2E1 in proportional to the administration period. Specially, the sixth and seventh group which were administered for 2 and 3 days, respectively showed such a significant effect in decreasing the protein expression that the expression is lower than that of the control group.

(2) Enzyme activity

In order to examine the effect of the compound of the present invention on the activity of the enzymes involved in phase I reaction, the experiments were carried out as follows:

(2-1) p-Nitrophenol hydroxylase

Six groups of Sprague-Dawley rat weighing 190±30 g were administered with pyrazine(Groups 1 to 3) or the compound prepared in Example 1-1(Groups 4 to 6) in a dose of 200 mg/kg for 1, 2 or 3 days. After the hepatic microsomes were separated by following the same procedure as in the above (1), activity of p-nitrophenol hydrolase was measured according to the method of Koop(Dennis R. Koop, Hydroxylation p-nitrophenol by rabbit ethanol inducible cytochrome P-450 isozyme 3a, Molecular Pharmacol. 29, 399–404(1986)).

Thus, 1 mg of microsomes and 1mM p-nitrophenol were added to 0.6 ml of 0.1M potassium phosphate buffer(pH 6.8) to make the total volume of 0.9 ml. The resulting mixture was preliminarily reacted in a 37° C. incubator for 2 minutes and started to react while adding 1 mM NADPH(0.1 ml). After 3 minutes, 0.5 ml of 0.6N perchloric acid was added to develop a color and the absorbance at 546 nm was measured at once. The enzyme activity was expressed in terms of mole concentration of 4-nitrocatechol, the product of reaction for 1 minute.

Figure 2:
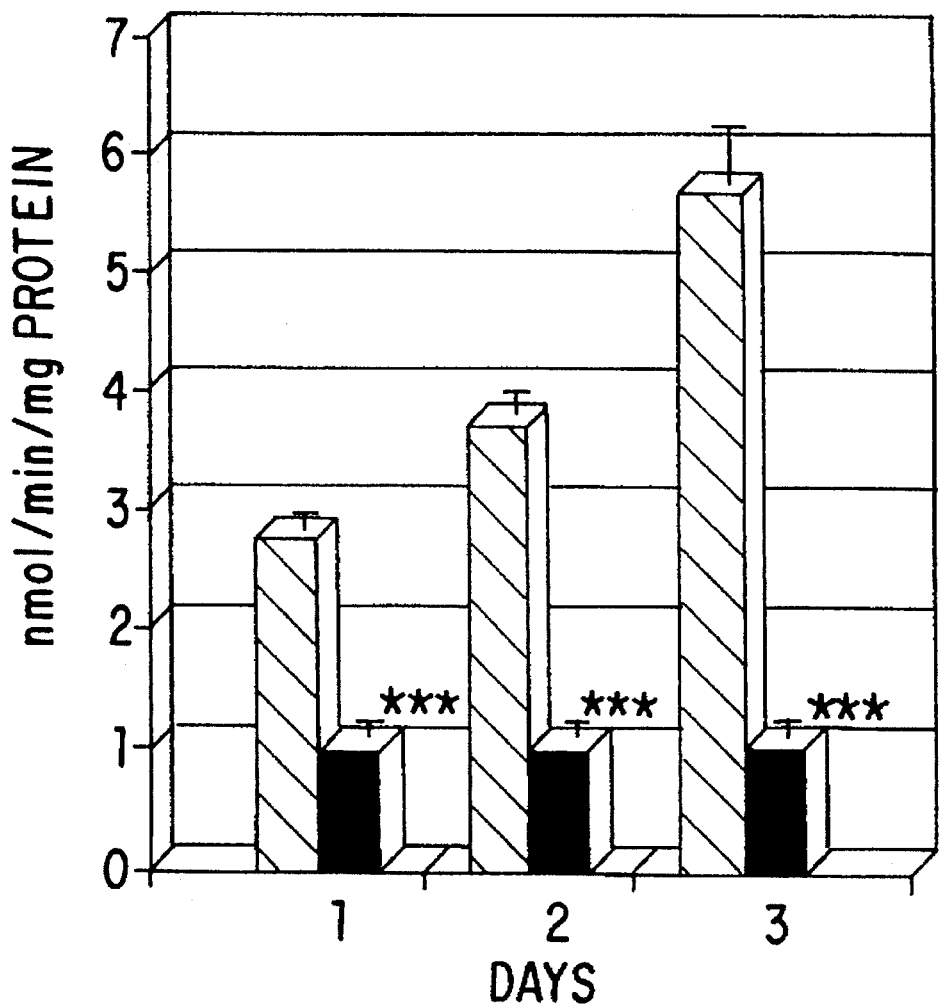
FIG. 2 shows time dependent changes in p-nitorphenol hydroylase activity following treatment with pyrazine and the present compound (Experimental Example 1(2-1)).

The results are shown in FIG. 2. In FIG. 2, the sign "★" means a significant difference of each individual, and "★", "★★" and "★★★" indicate $p<0.05$, $p<0.01$ and $p<0.001$, respectively. This is the same for all FIGS. As can be seen from FIG. 2, Groups 4 to 6(received the present compound) decrease the activity of p-nitrophenol hydrolase by 64%, 73% and 82% compared to Groups 1 to 3(received pyrazine) for 1, 2 and 3 days' administration, respectively.

(2-2) Aniline hydroxylase

The same procedure as in the above (2-1) was carried out to measure the activity of aniline hydroxylase. The activity of aniline hydroxylase was measured according to the method of Mieyal(John J. Mieyal, Acceleration of the autooxidation of human oxyhemoglobin by aniline and its relation to hemoglobin-catalyzed aniline hydroxylation, J. Biol. Chem. 251, 3442–3446(1976)).

Thus, 1 mg of microsomes and 5 mM aniline were added to 0.6 ml of 0.1M potassium phosphate buffer(pH 6.8) to make the total volume of 0.9 ml. 1 mM NADPH was added to make the total volume of 1.0 ml and the resulting mixture was reacted at 37° C. After 10 minutes, 20% trichloroacetic acid was added to stop the reaction and the reaction mixture was centrifuged. To 1 ml of supernatant were added 0.1 ml of 5% phenol and 0.1 ml of 2.5N sodium carbonate, dissolved in 0.1N NaOH. The mixture was allowed to stand for 30 minutes to develop a color and the absorbance at 630 nm was measured at once. The enzyme activity was expressed in terms of mole concentration of 4-aminophenol, the product of reaction for 1 minute.

Figure 3:
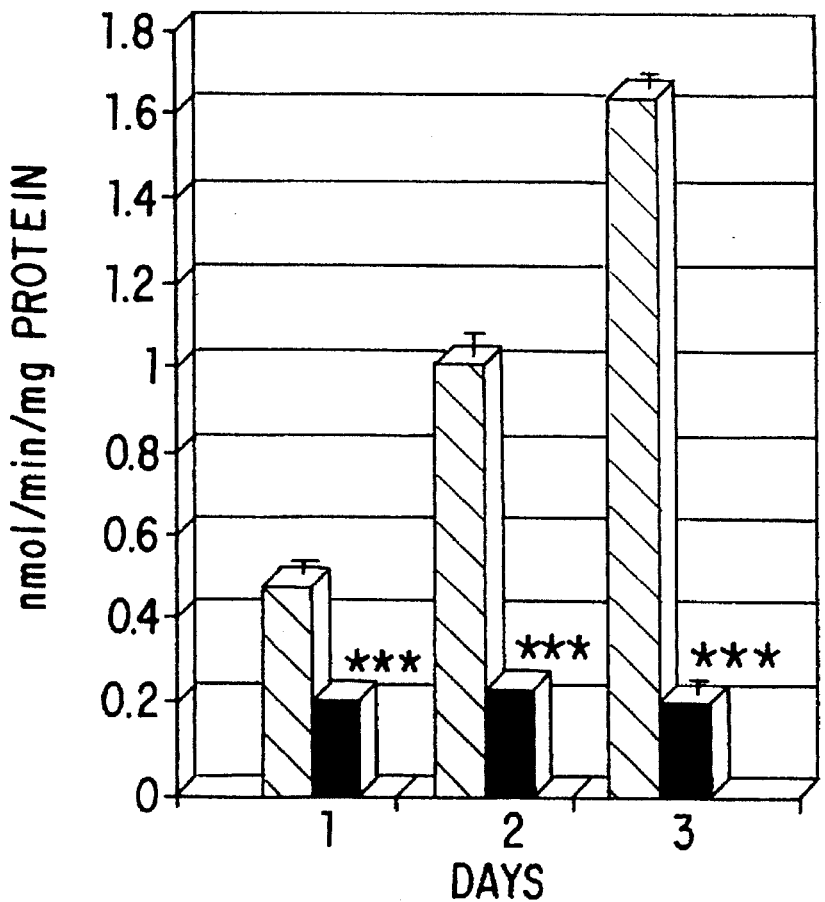
FIG. 3 shows time dependent changes in aniline hydroxylase activity following treatment with pyrazine and the present compound(Experimental Example 1(2-2)).

The results are shown in FIG. 3. As can be seen from FIG. 3, Groups 4 to 6(received the present compound) decrease the activity of aniline hydroxylase by 57%, 80% and 88% compared to Groups 1 to 3(received pyrazine) for 1, 2 and 3 days' administration, respectively.

(2-3) N-Nitrosodimethylamine demethylase

The same procedure as in the above (2-1) was carried out to measure the activity of N-nitrosodimethyl demethylase. The activity of N-nitrosodimethyl demethylase was measured according to the method of Kaul and Novak(Kaul, L. L. and Novak, R. F., Induction of rabbit hepatic microsomal cytochrome P-450 by imidazole; enhanced metabolic activity and altered substrate specificity, Arch. Biochem. Biophys., 235, 470–481(1984)).

Thus, 10 mM N-Nitrosodimethylamine and 0.6 ml of 0.1M potassium phosphate buffer(pH 7.4) were added to 1 mg of microsomes, and 1 mM NADPH was added to make the total volume of 1 ml. After the mixture was reacted at 37° C. for 30 minutes, 20% trichloroacetic acid was added to stop the reaction and the reaction mixture was centrifuged. To 0.75 ml of supernatant was added Nash reagent (ammonium acetate 15.416 g, acetylacetate 0.206 ml and acetic acid 0.289 ml in 100 ml of distilled water). The mixture was allowed to stand at 37° C. for 45 minutes to develop a color and the absorbance at 412 nm was measured. The enzyme activity was expressed in terms of mole concentration of formaldehyde produced from the reaction for 1 minute.

Figure 4:
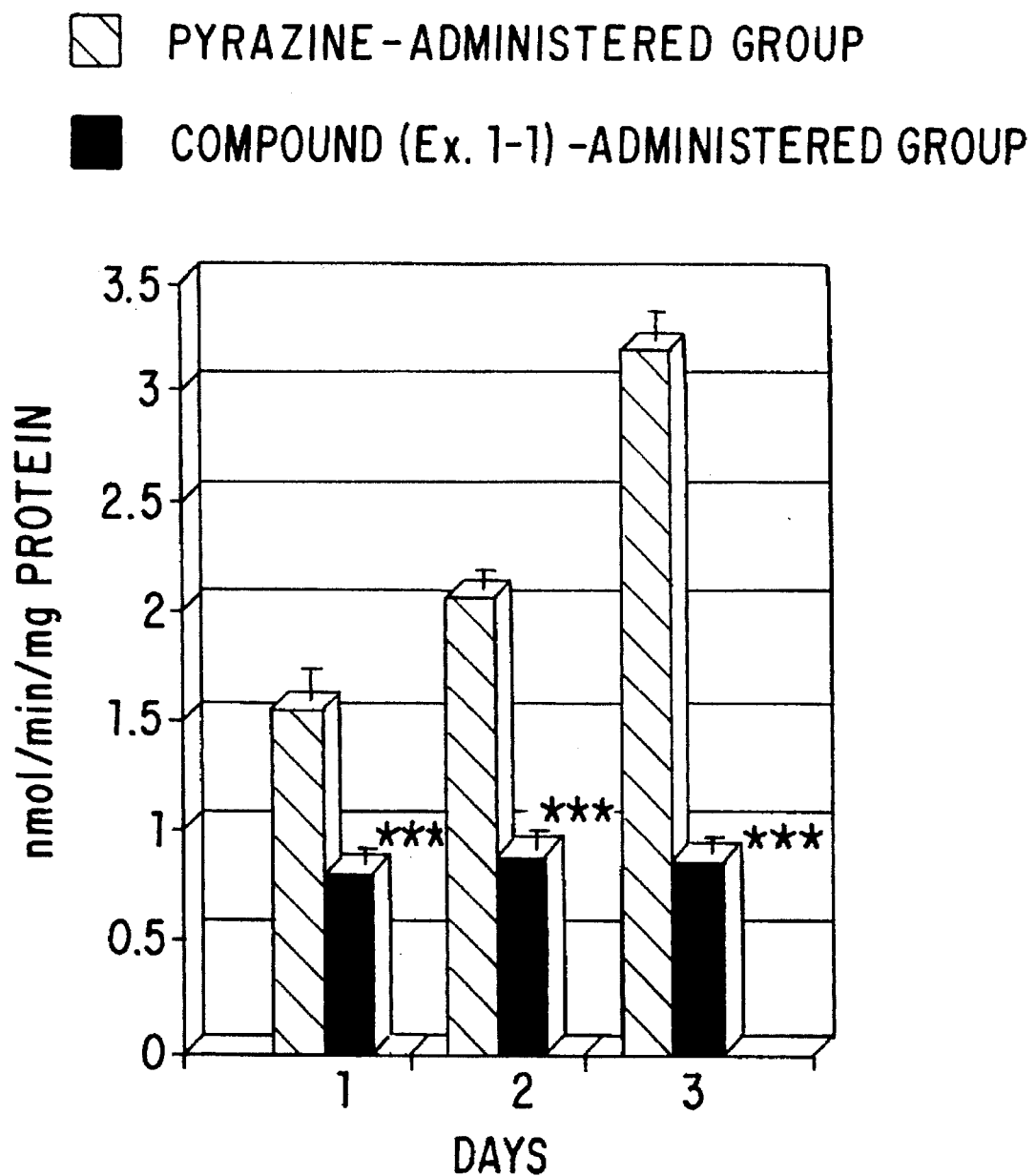
FIG. 4 shows time dependent changes in N-nitrosodimethylamine demethylase activity following treatment with pyrazine and the present compound (Experimental Example 1(2-3)).

The results are shown in FIG. 4. As can be seen from FIG. 4, Groups 4 to 6(received the present compound) decrease in a time-dependent manner the activity of N-nitrosodimethylamine demethylase by 49–73% compared to Groups 1 to 3(received pyrazine) in proportional to the period of administration.

EXPERIMENTAL EXAMPLE 2

Inhibition of the phase I reaction(2)

(1) Immunoblot analysis

In order to examine the effect of the compounds of the present invention on the expression of the enzymes involved in phase I reaction when administered together with isoniazid(INAH), an inducer of the enzyme system involved in phase I reaction, the immunoblot analysis was carried out as follows:

36 Male sprague-Dawley rat weighing 190±30 g were divided into 9 groups. To the first group as a control group, corn oil was administered intraperitoneally in an amount of 0.1 ml/200 g body weight. The second group was administered intraperitoneally INAH diluted with PBS in a dose of 200 mg/kg body weight. The third to ninth groups were administered intraperitoneally INAH diluted with PBS in a dose of 200 mg/kg body weight and then administered intraperitoneally the compounds of Examples 2 to 8, respectively, which are diluted with corn oil in a dose of 200 mg/kg body weight. The hepatic microsomes were separated and subjected to Western blot analysis on SDS-PAGE by following the same procedure as in the above Experimental Example 1 (1).

The results are shown in FIG. 5. As can be seen from FIG. 5, the third to ninth groups(lanes 3 to 9) receiving INAH plus the inventive compound show weak bands, indicating the inventive compounds suppress the enzyme expression induced by the action of INAH. The ninth group received the compound of Example 8 shows the strongest suppression.

(2) Enzyme activity

In order to examine the effect of the compound of the present invention on the activity of the enzymes involved in phase I reaction when administered in combination with INAH, the experiments were carried out as follows:

Eight groups of Sprague-Dawley rat weighing 190±30 g were intraperitoneally administered with INAH(Group 1), or INAH plus the compounds of Examples 2 to 8(Groups 2 to 8), each in a dose of 200 mg/kg. The inventive compounds and INAH were diluted with corn oil and PBS respectively, and the test compounds were administered just after administering INAH.

The changes in the activity of p-nitrophenol hydroxylase and aniline hydroxylase were measured by following the same procedure as in Experimental Example 1(2-1) and (2-2). The activity of enzymes was determined by considering the activity of enzyme when INAH alone was administered as 100%. The results are shown in Table 2.

TABLE 2

| Group | Enzymes | |
|---|---|---|
| | Amount (nmol/min/mg protein) | Activity (%) |
| p-Nitrophenol hydrolase | | |
| 1. INAH | 5.80 | 100 |
| 2. INAH + Compd (Ex. 2) | 4.52 | 78 |
| 3. INAH + Compd (Ex. 3) | 4.23 | 73 |
| 4. INAH + Compd (Ex. 4) | 3.69 | 64 |
| 5. INAH + Compd (Ex. 5) | 3.53 | 61 |
| 6. INAH + Compd (Ex. 6) | 3.25 | 56 |
| 7. INAH + Compd (Ex. 7) | 2.33 | 40 |
| 8. INAH + Compd (Ex. 8) | 2.33 | 40 |
| Aniline hydroxylase | | |
| 1. INAH | 1.453 | 100 |
| 2. INAH + Compd (Ex. 2) | 1.070 | 74 |
| 3. INAH + Compd (Ex. 3) | 1.108 | 76 |
| 4. INAH + Compd (Ex. 4) | 0.972 | 67 |
| 5. INAH + Compd (Ex. 5) | 0.972 | 67 |
| 6. INAH + Compd (Ex. 6) | 0.879 | 60 |
| 7. INAH + Compd (Ex. 7) | 0.712 | 49 |
| 8. INAH + Compd (Ex. 8) | 0.659 | 45 |

As can be seen from Table 2, the compounds of the invention inhibit the expression of p-nitrophenol hydroxylase and aniline hydroxylase induced by INAH. Particularly, the compounds of Examples 7 and 8 show a superior inhibitory action.

EXPERIMENTAL EXAMPLE 3

Induction of the phase II reaction(1)

(1) Western blot analysis

In order to examine the effect of the compounds of the present invention on the expression of the enzymes involved in phase II reaction, the western blot analysis was carried out as follows:

28 Male sprague-Dawley rat weighing 190±30 g were divided into 7 groups. To the first group as a control group, 0 ml of corn oil per 200 g body weight was administered intraperitoneally. The second to fourth groups were administered intraperitoneally pyrazine diluted with corn oil in a dose of 200 mg/kg body weight for 1, 2 or 3 days, respectively. The fifth to seventh groups were administered intraperitoneally the compound prepared in Example 1-1, which is diluted with corn oil in a dose of 200 mg/kg body weight for 1, 2 or 3 days, respectively.

The hepatic microsomes were separated and subjected to SDS-polyacrylamide gel electrophoresis by following the same procedure as in the above Experimental Example 1(1). Thereafter, western blot analysis for microsomal epoxide hydrolase(mEH) was carried out as follows:

5 μl of Rabbit anti-rat epoxide hydrolase IgG was mixed with 15 ml of PBS and placed into a bag containing the electrophoresed nictrocellulose paper, which was shaken for 2 hours. 15 μl of Biotinylated donkey anti-goat IgG, as the second antibody, in 15 ml of PBS was added to the nitrocellulose paper and reacted for 2 hours. Streptavidine-horseradish peroxidase and 4-chloro-1-naphtol were added to the reaction mixture to develop a color.

Figure 6:
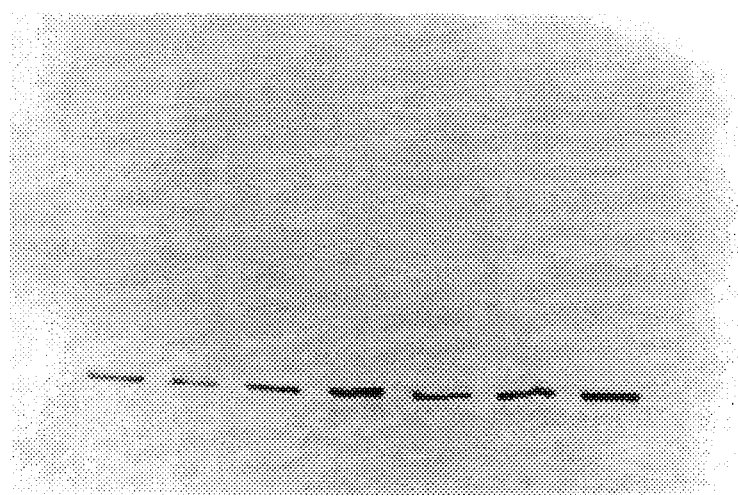
FIG. 6 is immunoblot analyses of hepatic microsomes isolated from rats treated with corn oil, pyrazine and the present compound with anti-mEH antibody(Experimental Example 3(1)).

The results are shown in FIG. 6. The fifth to seventh groups, which received the compound of the invention showed a significant increase in the expression of mEH compared to the first(control) or the second to fourth groups which received pyrazine. Specially, the sixth and seventh group, which were administered with the inventive compound for 2 and 3 days, respectively, increase the expression of mEH by 4 to 5 times in proportional to the administration period.

(2) Enzyme activity

In order to examine the effect of the compound of the present invention on the activity of glutathione S-transferase (GST), an enzymes involved in phase II reaction, the experiments were carried out as follows:

Nine(9) groups of Sprague-Dawley rat weighing 190±30 g were administered with corn oil(Groups 1 to 3), pyrazine (Groups 4 to 6) or the compound prepared in Example 1-1(Groups 7 to 9) in a dose of 200 mg/kg for 1, 2 or 3 days. And tenth group was administered with pyrazine plus the compound prepared in Example 1-1 in a dose of 200 mg/kg for 3 days. After the hepatic microsomes were separated by following the same procedure as in the Experimental Example 1(1), cytosolic activity of GST was measured according to the method of Habig(Habig, W. H., J. Biol. Chem. 249, 7130–7139(1974)).

Thus, to 25 μg(0.1 ml) of cytosol protein were added 0.1 mM 1-chloro-2,4-nitrobenzene and 1.0 mM glutathione as substrates, and 0.1M potassium phosphate were added to make the total volume of 1.0 ml(pH 6.4). The resulting mixture was allowed to stand at room temperature for 2 minutes and measured for its absorbance at 340 nm at intervals of 15 seconds during the period of 1 minute. As a reference, a cytosol protein denatured by heating was used. The activity of GST was calculated by measuring the change of absorbance for the period of 1 minute and employing the extinction coefficient of 9.6 $mM^{-1}cm^{-1}$.

Figure 7:
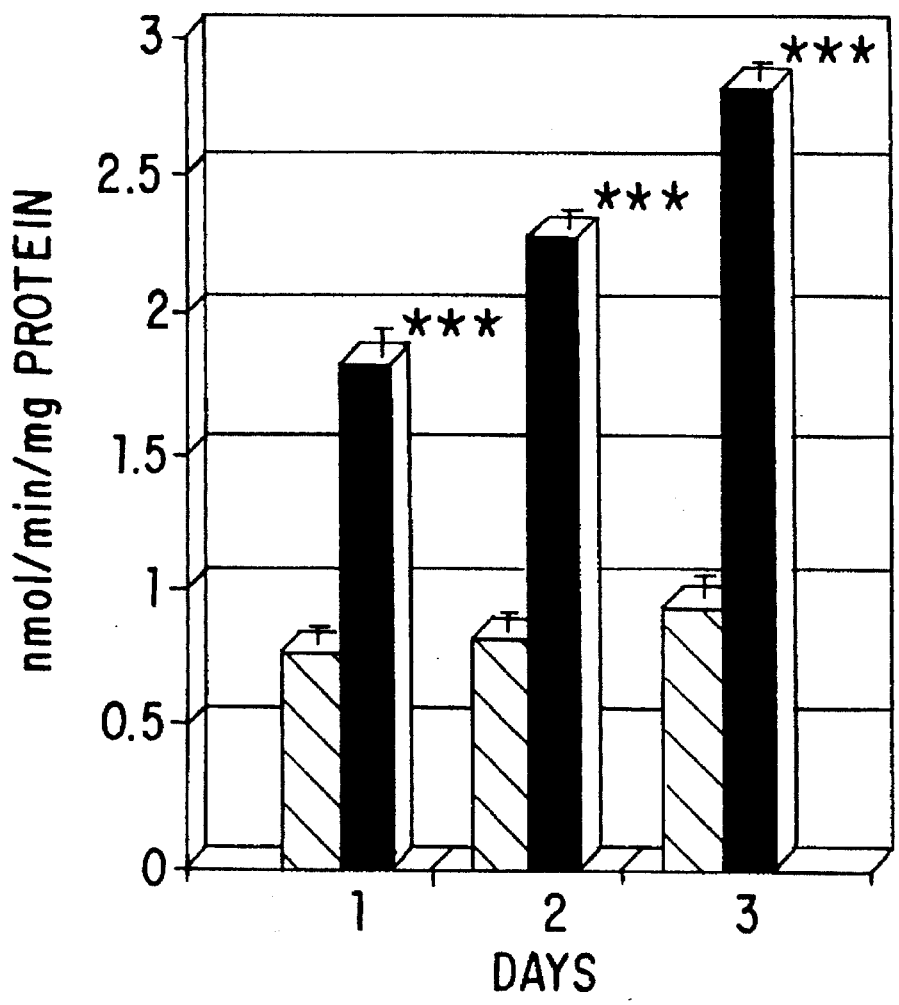
FIG. 7 shows time dependent changes in glutathione S-transferase activity following treatment with corn oil and the present compound(Experimental Example 3(2)).
Figure 8:
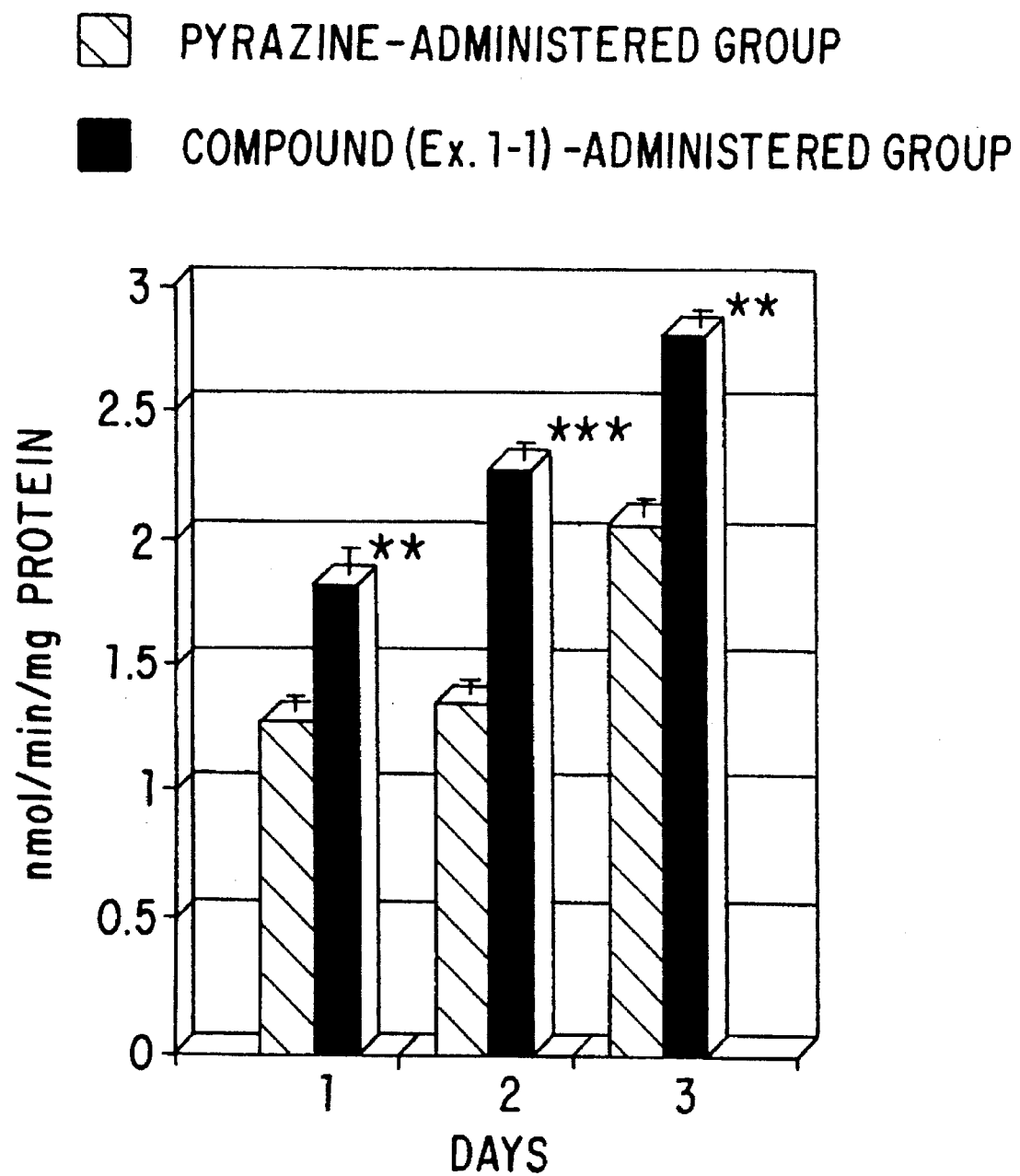
FIG. 8 shows time dependent changes in glutathione S-transferase activity following treatment with pyrazine and the present compound(Experimental Example 3(2)).
Figure 9:
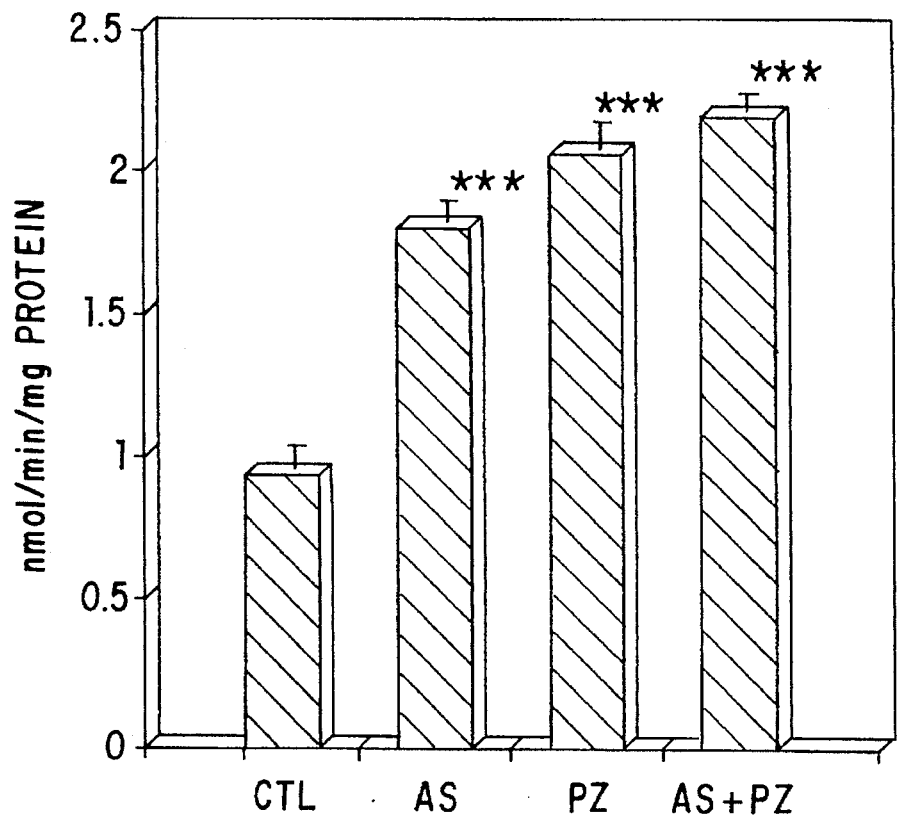
FIG. 9 shows glutathione S-transferase activity following treatment with corn oil, pyrazine, the present compound and pyrazine plus the present compound(Experimental Example 3(2)).

The results are shown in FIGS. 7 through 9. FIG. 7 is a bar graph comparing the results of the control groups with those of the groups received the inventive compound. FIG. 8 is a bar graph comparing the results of the groups received pyrazine with those of the groups received the inventive compound. FIG. 9 is a bar graph comparing the results of control group, and of 3 day administration of pyrazine, allylsulfide, and pyrazine plus the inventive compound.

As can be seen from FIGS. 7 through 9, the groups received the inventive compound increase in a time-dependent manner the GST activity by 135%, 178% and 200% for 1, 2 and 3 days' administration compared to the control groups, which are much higher than 130% and 140% increase by the groups received pyrazine- and pyrazine plus the inventive compound for 3 days. Therefore, the compound of the invention are effective in inducing the enzymes involved in phase II reaction.

EXPERIMENTAL EXAMPLE 4

Induction of the phase II reaction(2)

(1) Immunoblot analysis

In order to examine the effect of the compounds of the present invention on the expression of the enzymes involved in phase II reaction, the immunoblot analysis was carried out as follows:

32 Male sprague-Dawley rat weighing 190±30 g were divided into 8 groups. To the first group as a control group, 0.1 ml of corn oil per 200 g body weight was administered intraperitoneally. The second to eighth groups were administered intraperitoneally the compound of Examples 2 to 8 diluted with corn oil in a dose of 200 mg/kg body weight.

The hepatic microsomes were separated and subjected to Western blot analysis on SDS-PAGE by following the same procedure as in the above Experimental Example 1(1).

Figure 10:
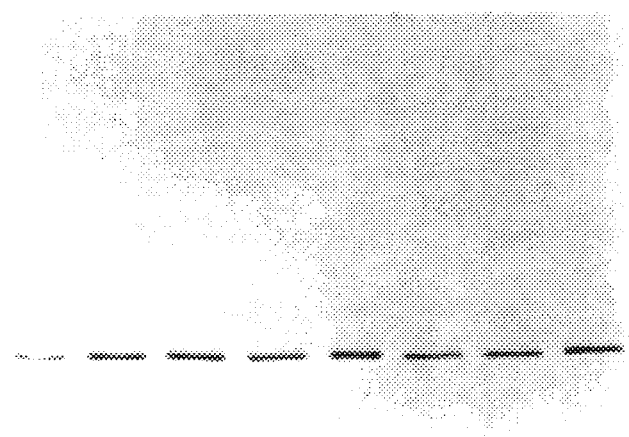
FIG. 10 is immunoblot analyses of microsomes isolated from rats treated with corn oil and the present compound with anti-mEH antibody(Experimental Example 4).

The results are shown in FIG. 10. As can be seen from FIG. 10, the second to eighth groups(lanes 2 to 8) received the inventive compound show strong bands, indicating the inventive compounds induces the enzyme expression.

(2) Enzyme activity

In order to examine the effect of the compound of the present invention on the activity of the enzymes involved in phase II reaction when administered alone or in combination with INAH, the experiments were carried out as follows:

Sixteen groups of Sprague-Dawley rat weighing 190±30 g were intraperitoneally administered with corn oil(Group 1), compounds of Examples 2 to 8(Groups 2 to 8), INAH (Group 9), or INAH plus the compounds of Examples 2 to 8(Groups 10 to 16), each in a dose of 200 mg/kg. The inventive compounds and INAH were diluted with corn oil, and the test compounds were administered just after administering INAH.

The change in the activity of GST was measured by following the same procedure as in Experimental Example 3(2). The activity of enzyme was determined by considering the activity of enzyme when corn oil or INAH alone was administered as 100%. The results are shown in Table 3.

TABLE 3

| Group | Enzymes Glutathion S-transferase | |
|---|---|---|
| | Amount (nmol/min/mg protein) | Activity (%) |
| 1. Corn oil (Control) | 1.725 | 100 |
| 2. Compd (Ex. 2) | 2.533 | 147 |
| 3. Compd (Ex. 3) | 2.708 | 157 |
| 4. Compd (Ex. 4) | 2.892 | 168 |
| 5. Compd (Ex. 5) | 2.996 | 174 |
| 6. Compd (Ex. 6) | 2.558 | 148 |
| 7. Compd (Ex. 7) | 3.046 | 177 |
| 8. Compd (Ex. 8) | 3.290 | 181 |
| 9. INAH | 2.008 | 100 |
| 10. INAH + Compd (Ex. 2) | 2.675 | 133 |
| 11. INAH + Compd (Ex. 3) | 3.071 | 153 |
| 12. INAH + Compd (Ex. 4) | 2.683 | 134 |
| 13. INAH + Compd (Ex. 5) | 3.029 | 151 |
| 14. INAH + Compd (Ex. 6) | 2.375 | 118 |
| 15. INAH + Compd (Ex. 7) | 2.263 | 113 |
| 16. INAH + Compd (Ex. 8) | 2.808 | 140 |

As can be seen from Table 3, the compounds of the invention induce the expression of glutathione S-transferase and particularly the compounds of Examples 5, 7 and 8 increase the expression of the enzyme by 70% or more. Further, the results in Table 3 show that, even when INAH, a inhibitor of the enzyme expression is administered, the compounds of the invention, particularly, the compounds of Examples 3, 5 and 8 strongly induce expression of enzyme.

To a conclusion, the compounds of the present invention can effectively inhibit the expression of enzymes involved in phase I reaction while activate the expression of enzymes involved in phase II reaction, thereby can be advantageously used to protect liver from being injured by various chemicals.

What is claimed is:

1. A compound having a following formula (I):

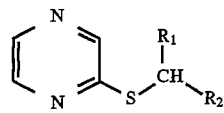

wherein, $R_1$ represents a hydrogen atom or a $C_{1-3}$ alkyl group; and $R_2$ represents a phenyl group or a group represented by the formula: —$C(R_a)$=$C(R_b)(R_c)$, wherein $R_a$, $R_b$ and $R_c$ being the same or different from each other, means a hydrogen atom, a methyl group or a phenyl group.

2. The compound claimed in claim 1, wherein $R_1$ is a hydrogen atom or a methyl group, and $R_2$ is a group represented by the formula: —$C(R_a)$=$C(R_b)(R_c)$, wherein $R_a$, $R_b$, and $R_c$, being the same or different from each other, means a hydrogen atom or a methyl group.

3. The compound claimed in claim 1, which is one selected from the group consisting of 2-(2-propenylthio)pyrazine, 2-(benzylthio)pyrazine, 2-(3-methyl-2-butenylthio)pyrazine, 2-(cinnamylthio)pyrazine, 2-(3-methyl-3-butenylthio)pyrazine, 2-(2-butenylthio)pyrazine and 2-(3-butenylthio)pyrazine.

4. A chemopreventive composition comprising as an active ingredient the compound of the formula (I):

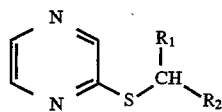

wherein, $R_1$ represents a hydrogen atom or a $C_{1-3}$ alkyl group; and $R_2$ represents a phenyl group, or a group represented by the formula: —$C(R_a)$=$C(R_b)(R_c)$, wherein $R_a$, $R_b$ and $R_c$ being the same or different from each other, means a hydrogen atom, a methyl group or a phenyl group, wherein said compound (I) inhibits phase I reaction enzymes to prevent the formation of activated toxic intermediate metabolites and induces phase II reactions to promote excretion of toxic substances, and a pharmaceutically acceptable carrier.

5. The compound as claimed in claim 1, wherein $R_2$ is a phenyl group.

6. The composition as claimed in claim 4, wherein $R_2$ is a phenyl group.

7. The composition as claimed in claim 4, wherein $R_1$ is a hydrogen atom or a methyl group, and $R_2$ is a group represented by the formula: —$C(R_a)$=$C(R_b)(R_c)$, wherein $R_a$, $R_b$, and $R_c$, being the same or different from each other, means a hydrogen atom or a methyl group.

* * * * *